United States Patent [19]
Piraka

[11] Patent Number: 6,077,284
[45] Date of Patent: Jun. 20, 2000

[54] LAPAROSCOPIC SCALPEL

[76] Inventor: Hadi A. Piraka, 21257 Woodfarm, Northville, Mich. 48167

[21] Appl. No.: 09/312,874

[22] Filed: May 17, 1999

[51] Int. Cl.[7] .................................................. A61B 17/32
[52] U.S. Cl. ............................................................. 606/167
[58] Field of Search .................................. 606/167, 159, 606/182, 185, 184; 604/204

[56] References Cited

U.S. PATENT DOCUMENTS

| | | | |
|---|---|---|---|
| 5,372,588 | 12/1994 | Farley et al. | 604/164 |
| 5,449,335 | 9/1995 | Rhum et al. | 606/41 |

*Primary Examiner*—Michael Buiz
*Assistant Examiner*—Vy Q. Bui
*Attorney, Agent, or Firm*—Alex Rhodes

[57] ABSTRACT

A scalpel which is used for enlarging an incision in an abdominal wall to remove an organ or body tissue from an abdominal or chest cavity through which a cannula is inserted. The scalpel has a split resilient generally cylindrical collar for mounting the scalpel on the cannula, a pair of sharp pointed cutting blades mounted on opposite sides of an outer surface of the collar and a pair of generally rectangular pusher arms pivotally mounted on the cutting blades. The pusher arms are rotatable from positions of outward extending relationship to the collar to positions of adjacent relationship to the collar. The incision is enlarged by mounting the scalpel on the cannula and applying a force to the pusher arms in outward extending positions to push the sharp cutting blades through the abdominal wall. If the blades do not fully penetrate the abdominal wall, the pusher blades are rotated in adjacent relationship and used to completely push the sharp cutting edges through the abdominal wall.

12 Claims, 3 Drawing Sheets

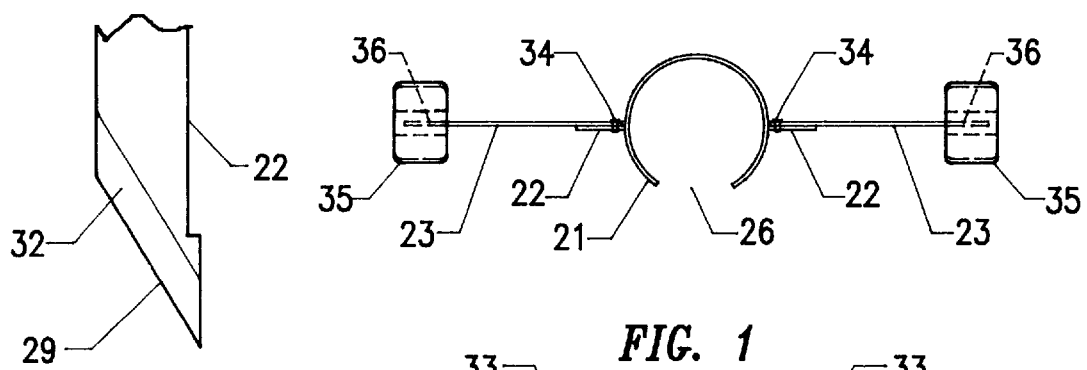
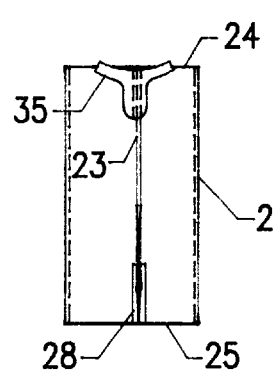
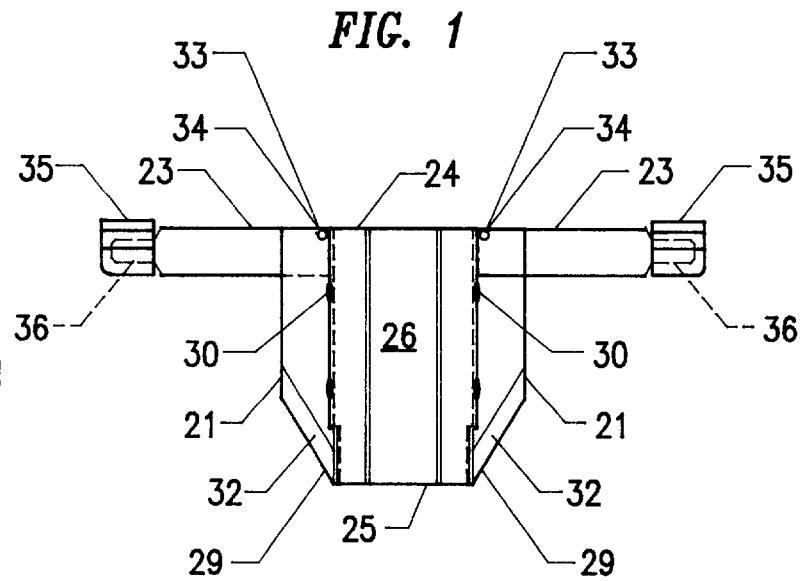
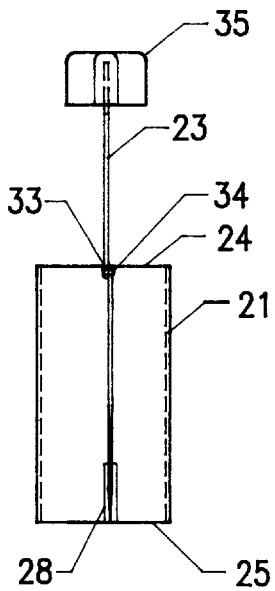
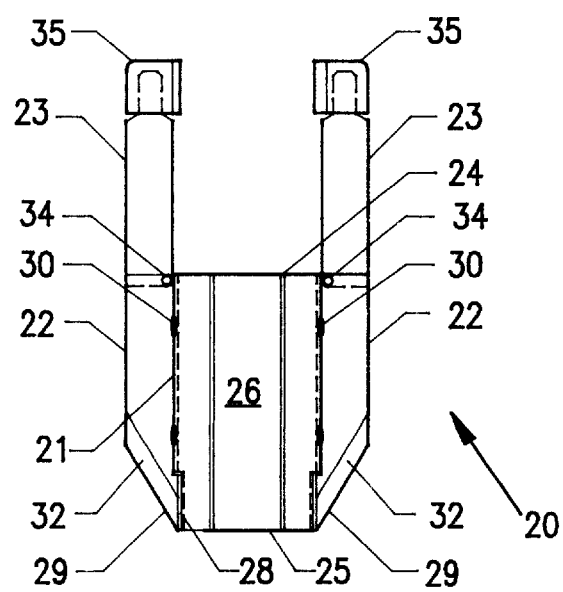
FIG. 6
FIG. 1
FIG. 3
FIG. 2
FIG. 5
FIG. 4

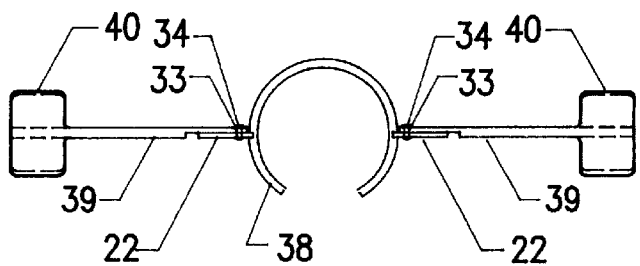
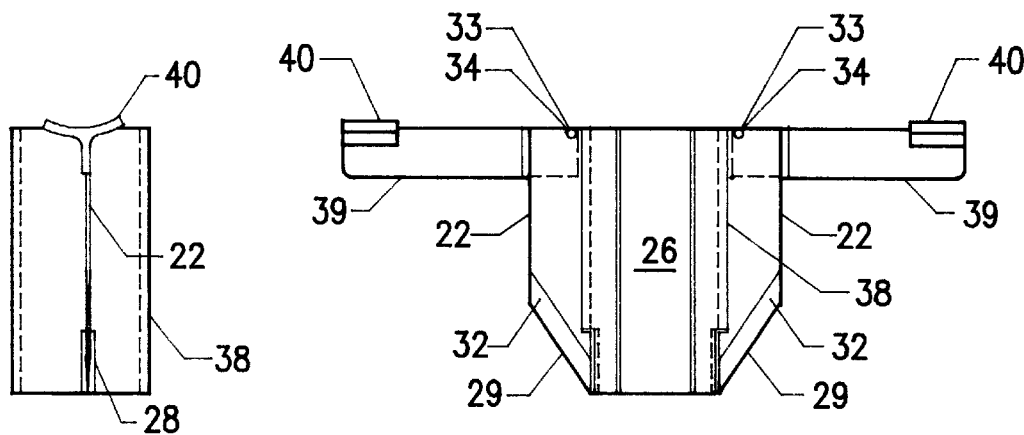
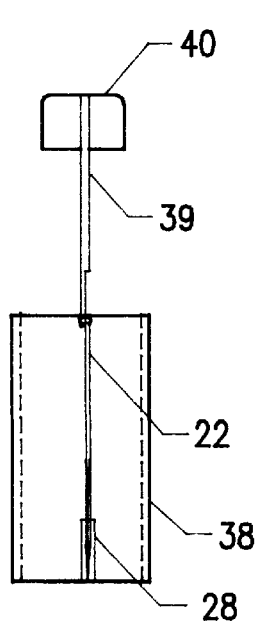
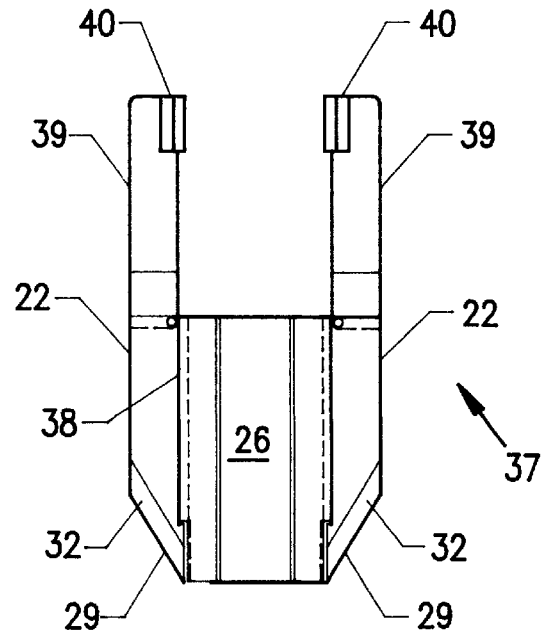

LAPAROSCOPIC SCALPEL

FIELD OF THE INVENTION

This invention relates to surgical scalpels and more particularly to a scalpel which is used for enlarging an incision to remove a diseased organ or body tissue during laparoscopic surgery.

BACKGROUND OF THE INVENTION

Small incisions are made during laparoscopic surgeries for inserting laparoscopes into abdomens and chest cavities. This is usually followed by small incisions for inserting instruments for grasping, cutting and removing diseased organs and body tissues. The task of removing a diseased body part or diseased tissue through an incision for a laparoscope is difficult because of the limited size of the incision.

During many laparoscopic procedures, an incision is enlarged with a conventional scalpel and/or scissor to facilitate the removal of a diseased organ or tissue. This technique is difficult, time consuming and imprecise. A further drawback is that an assistant is needed to retract the sides of an incision during the enlargement of the incision.

To overcome these drawbacks, a diseased organ or body tissue is sometimes deposited in a laparoscopic bag and forcibly pulled through an incision. The laparoscopic bag is sometimes torn during its forcible removal, causing entrapment and/or rupture of the excised organ as well as spillage inside a body cavity. Spillage may cause infection, cancer or chemical irritation.

Heretofore, special techniques or devices have not been available to facilitate the removal of a diseased organ and tissue during laparoscopic surgery.

SUMMARY OF THE INVENTION

The difficulties and drawbacks which are encountered when removing diseased body parts during laparoscopic surgery are completely overcome with the present invention. This is accomplished by mounting a novel scalpel on a cannula which is used for performing the laparoscopic surgery. The novel scalpel provides an enlarged, clean, precise incision for removing the diseased organ or body tissue without disrupting the laparoscopic procedure. The precise incision reduces the trauma to a patient and the time for performing a laparoscopic surgery.

The scalpel is comprised of a pair of sharp blades attached to a split cylindrical collar and a pair of pusher arms pivotally attached to the blades. The collar is mounted on a cannula and the blades are used for enlarging the incision in which the cannula is inserted. To enlarge the incision the blades are pushed through the abdominal wall into an abdominal or chest cavity. Initially, the pusher arms are perpendicular to the blades. If the blades do not fully enter the cavity, the pusher arms are rotated to aligned relationship with the blades and push the blades through the abdominal wall.

After the blades have passed through the abdominal wall they are withdrawn with the cannula and body part. During the withdrawal, the pusher arms guide the blades and prevent damage to adjacent tissues.

In employing the teaching of the present invention, a plurality of alternate constructions can be adopted to achieve the desired results and capabilities. In this disclosure, only two preferred embodiments are discussed which are intended as examples, and should not be considered as limiting the scope of the invention.

Further features and benefits will become apparent by reference to the drawings and ensuing detailed description of a preferred embodiment which discloses the best mode contemplated in carrying out the invention. The exclusive rights which are claimed are set forth in each of the numbered claims following the detailed description of the preferred embodiment.

BRIEF DESCRIPTION OF THE DRAWINGS

The invention will be better understood and further objects, characterizing features, details and advantages thereof will appear more clearly with reference to the diagrammatic drawings illustrating specific embodiments of the invention by way of non-limiting example only.

FIG. 1 is a plan view of a laparoscopic scalpel with a pair of pusher arms extending outwardly in perpendicular relationship to a pair of cutting blades.

FIG. 2 is a front view of the laparoscopic scalpel.

FIG. 3 is a right side view of the laparoscopic scalpel.

FIG. 4 is a front view of the laparoscopic scalpel with the pusher arms rotated upwardly in aligned relationship with the cutting blades.

FIG. 5 is a right side view of FIG. 4.

FIG. 6 is an enlarged partial view of one of the blades.

FIG. 7 is a plan view of a second embodiment of my laparoscopic scalpel with a pair of cutting blades extending outwardly in perpendicular relationship with a pair of cutting blades.

FIG. 8 is a front view of FIG. 7.

FIG. 9 is a right side view of FIG. 7.

FIG. 10 is a front view of the second embodiment with the pusher arms rotated upwardly in aligned relationship with the cutting blades.

FIG. 11 is a right side view of FIG. 10.

DETAILED DESCRIPTION OF A PREFERRED EMBODIMENT

Figure 12:
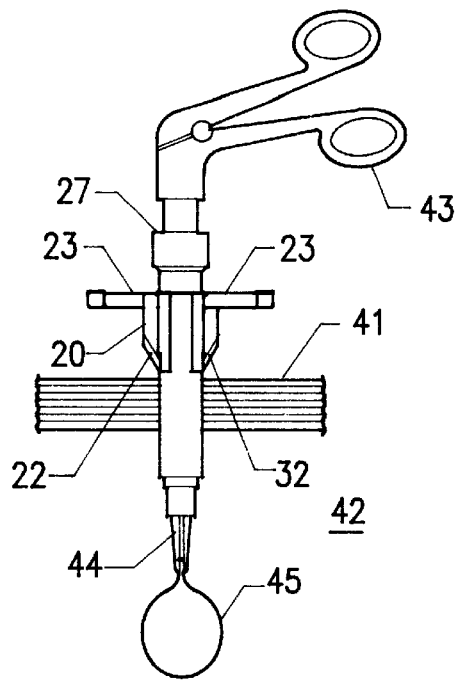
FIG. 12 shows the laparoscopic scalpel mounted on a cannula which is inserted through an abdominal wall.

Referring now to the drawings wherein like numerals designate like and corresponding parts, in FIGS. 1 through 6, inclusive, a scalpel 20 is shown for enlarging an incision at a laparoscopic site. The scalpel 20 is comprised of a cylindrical collar 21, a pair of thin cutting blades 22 mounted on the collar 21, and a pair of pusher arms 23 pivotally attached to the cutting blades 22.

The collar 21 is a split cylindrical part with parallel upper 24 and lower 25 edges. It is formed by incompletely forming a thin strip of spring steel into a cylinder, leaving a gap 26 between the ends of the strip. The gap 26 allows the collar 21 to be installed on a cannula 27 by spreading apart the ends of the strip. At one lower end portion of the collar 21 is a pair of notches 28 which receive pointed end portions 29 of the pair of cutting blades 22.

The pair of cutting blades 22 are joined to the outer surface of the collar 21 by solder, braze or resistance welds 30. The shape of the blade's pointed end portions 29 is depicted in FIG. 6. Extending along the pointed end portions 29 are sharp angular cutting edges 32. With reference to FIGS. 2 and 6, the pointed end portions 29 extend through the notches 28 such that the pointed ends of the blades 22 are opposite the inner surface of the collar 21. The width of the blades 22 is determined by the size of the organ or amount of tissue to be removed. Thus, it is contemplated that optional scalpels 20 differing blade widths will be available which embody the invention.

At an upper inner end portion of each blade 22, is an aperture 33 for pivotally attaching the pusher arm 23. The pusher arms 23 are pivotally attached to the blades 22 with rivets 34 or other suitable fasteners. The widths of the pusher arms 23 are preferably about the same as the blades 22. The use of the pusher arms 23 will be described in proper sequence.

With reference to FIGS. 1 and 2, on end portions of the pusher arms 23 are finger tabs 35. The finger tabs 35 are molded plastic parts and are retained to the pusher arms 23 engaging slots 36 of the finger tabs 35 with the ends of the pusher arms 23.

An alternate embodiment 38 is shown in FIGS. 7 through 11, inclusive, wherein a collar 38 is molded from a resilient plastic material and blades 22 are bonded to the collar 38 during a molding of the collar 38. Molded plastic pusher arms 39 with integral finger tabs 46 are pivotally attached to the blades 22 with rivets 34.

The manner of using my invention is shown in FIGS. 12 through 15, inclusive. In FIG. 12 the laparoscopic scalpel 20 is mounted on a cannula 27 by spreading apart and passing collar 21 over the cannula 27. The pusher arms 23 extend outwardly in perpendicular relationship to the cutting blades 22. The cannula 27 is shown extending through an abdominal wall 41 into a body cavity 42. A pair of laparoscopic forceps 43 are in the cannula 27 and the forceps' jaws 44 grasp an appendage of an organ 45 in the body cavity 42. The organ 45 is shown as being substantially larger than the opening through which the cannula 27 passes, requiring an enlargement of the opening.

Figure 13:
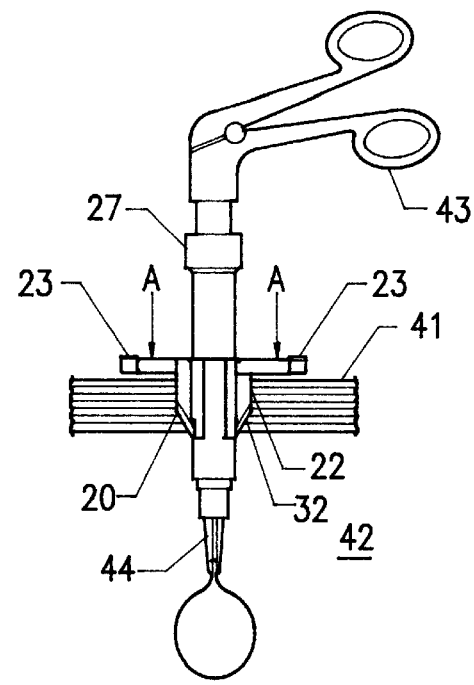
FIG. 13 shows the cutting blades pushed through a portion of the abdominal wall.

The initial step for enlarging the opening by extending the incision is shown in FIG. 13. The incision is extended by applying a force "A" to the pusher arms 23 to push the cutting edges 32 through the abdominal wall 41. However, as shown in FIG. 13, the cutting edges 32 are not completely through the abdominal wall 41.

Figure 14:
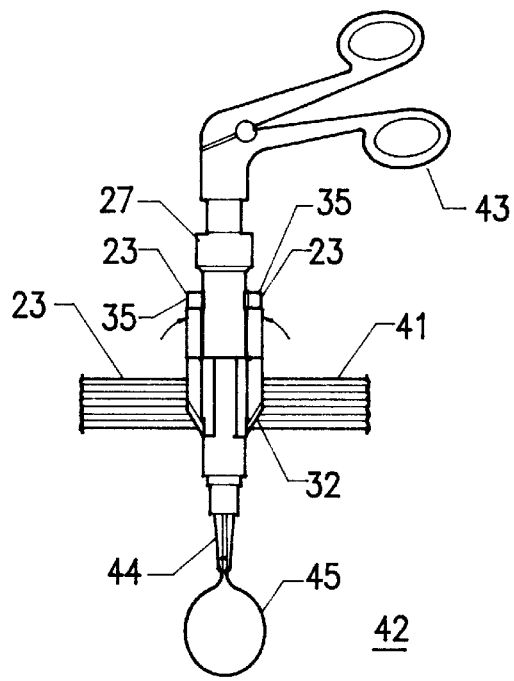
FIG. 14 shows the pusher arms rotated upwardly to aligned relationship with the cutting blades.
Figure 15:
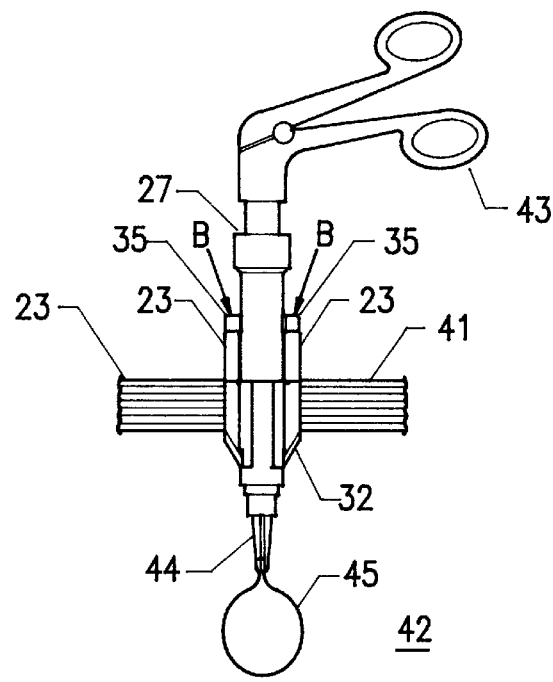
FIG. 15 shows the cutting blades completely pushed through the abdominal wall.

Referring now to FIG. 14, to fully pass the cutting edges 32 through the abdominal wall 41, the pusher arms 23 are rotated upwardly to aligned relationships with the cutting blades 22, and a force "B" is applied to the finger tabs 35. As shown in FIG. 15, the cutting edges 32 are through the abdominal wall 41.

After the cutting edges 32 have passed through the abdominal wall 41, as shown in FIG. 15, the scalpel 20 is withdrawn together with the organ 45 and cannula 27 from the abdominal wall 41. During the withdrawal, the blades 22 are guided along the same path as their insertion by the pusher arms 23, avoiding damage to adjacent tissues. Thus, the pusher arms 23 have several functions, i.e., to push the blades 22 into the body cavity 42, guide the blades 22 during a withdrawal, and to prevent damage to adjacent tissues.

From the foregoing it will be appreciated that my invention provides improvements heretofore unavailable for removing diseased organs and tissues through laparoscopic openings without injuries to adjacent tissues.

It will be appreciated that other embodiments can be developed by changes in shape, material, arrangement of parts, and substitution of parts without departing from the spirit thereof.

I claim:

1. A scalpel for enlarging an incision to facilitate a removal of an organ or body tissue through an incision made for inserting a laparoscope into a body cavity, comprising: a generally cylindrical collar defining an axis for mounting said laparoscopic scalpel on a cannula; at least one generally rectangular cutting blade aligned with said axis of said collar, said cutting blade attached to a side portion of said collar and having a sharp cutting edge portion.

2. The scalpel as recited in claim 1 further comprising a second rectangular cutting blade aligned with said axis of said collar, said second cutting blade attached to a side portion of said collar opposite said other cutting blade and having a sharp cutting edge portion.

3. The scalpel as recited in claim 1 further comprising a generally rectangular pusher arm pivotally attached to said cutting blade at an end portion opposite said cutting edge end portion, said pusher arm being rotatable from a position extending outwardly from said collar to a position which is aligned with said cutting blade.

4. The scalpel as recited in claim 3 further comprising a finger tab attached to an end portion of said pusher arm.

5. The scalpel as recited in claim 1 wherein said collar is a split collar for mounting said collar on a cannula, said collar being formed from a strip of spring steel and having a first pair of parallel edge portions which are perpendicular to said axis and a second pair of spaced apart parallel edge portions which are parallel to said axis.

6. The scalpel as recited in claim 1 wherein said collar is a split collar for mounting said collar on a cannula, said collar being molded from a resilient plastic material and having a first pair of parallel edge portions which are perpendicular to said axis and a second pair of spaced apart parallel edge portions which are parallel to said axis.

7. The scalpel as recited in claim 1 further comprising a generally rectangular pusher arm pivotally attached to said cutting blade at an end portion opposite said cutting edge end portion, said pusher arm having an enlarged tab end portion and being rotatable from a position extending outwardly from said collar to a position which is adjacent to said collar.

8. In combination with a cannula for removing an organ or body tissue from a body cavity, a scalpel mounted on said cannula for enlarging an incision through which said cannula passes into said body cavity, said scalpel comprising: a cylindrical collar, said collar defining an axis which is coincident with an axis of said cannula; and a pair of cutting blades attached to opposite side portions of said collar for enlarging said incision, each of said cutting blades having a pointed end portion and a sharp cutting edge extending along an angular edge of said pointed end portion.

9. The combination set forth in claim 8 further comprising a pair of pusher arms, each of said pusher arms being pivotally attached to one of said cutting blades and being rotatable from a position which is perpendicular to said axis to a position which is parallel to said axis.

10. The combination set forth in claim 9 wherein said collar is a split resilient collar for mounting and retaining said collar to said cannula.

11. A scalpel for removing an organ or body tissue from a body cavity by enlarging an incision through which a cannula passes into said body cavity, said scalpel comprising: a split generally cylindrical collar for mounting said scalpel on said cannula, a pair of cutting blades attached to opposite sides of an outer surface of said collar, each of said cutting blades having a sharp angular cutting edge; and a pair of generally rectangular pusher arms, each of said pusher arms being rotatable from a position in outward extending relationship to said collar to a position in adjacent relationship to said collar.

12. The scalpel as recited in claim 11 wherein one end of said collar has a pair of notches, said pointed end portions of said blades extending through said notches.

\* \* \* \* \*